United States Patent
Johansen

(10) Patent No.: US 6,862,094 B2
(45) Date of Patent: Mar. 1, 2005

(54) IMAGING SPR APPARATUS

(75) Inventor: Knut Johansen, Linköping (SE)

(73) Assignee: Spring Systems AB, Linkoping (SE)

(*) Notice: Subject to any disclaimer, the term of this patent is extended or adjusted under 35 U.S.C. 154(b) by 147 days.

(21) Appl. No.: 10/220,304

(22) PCT Filed: Mar. 14, 2001

(86) PCT No.: PCT/SE01/00530
§ 371 (c)(1),
(2), (4) Date: Sep. 13, 2002

(87) PCT Pub. No.: WO01/69209
PCT Pub. Date: Sep. 20, 2001

(65) Prior Publication Data
US 2003/0048452 A1 Mar. 13, 2003

Related U.S. Application Data

(60) Provisional application No. 60/189,084, filed on Mar. 14, 2000.

(51) Int. Cl.⁷ .............................................. G01N 21/55
(52) U.S. Cl. ...................................................... 356/445
(58) Field of Search ................................. 356/445–446

(56) References Cited

U.S. PATENT DOCUMENTS 6,600,563 B1 * 7/2003 Bahatt et al. ................ 356/445

FOREIGN PATENT DOCUMENTS

| WO | WO 9834098 A1 | 8/1998 |
| WO | WO 9930135 A1 | 6/1999 |

* cited by examiner

Primary Examiner—Gregory J. Toatley, Jr.
Assistant Examiner—Amanda Merlino
(74) Attorney, Agent, or Firm—Bacon & Thomas

(57) ABSTRACT

A two-dimensional imaging surface plasmon resonance (SPR) apparatus for optical surface analysis of a sample area on a sensor surface is disclosed. The apparatus comprises a sensor surface layer of a conductive material that can support a surface plasmon, such as a free electron metal, e.g. gold, silver or aluminum, a source of electromagnetic beams of two or more wavelengths that illuminate a two-dimensional surface area from either the front or the back-side of the sensor surface layer, and a detector for simultaneous, or pseudo simultaneous, detection of two or more wavelengths of reflected intensities from the two-dimensional surface area, providing two or more two-dimensional images of the surface area, the two-dimensional images being a function of the effective refractive index at each point on the surface area. The two-dimensional images put together result in a color image. The apparatus is suitable for use in biological, biochemical, chemical and physical testing.

22 Claims, 21 Drawing Sheets

751 nm 692 nm 634 nm

IMAGING SPR APPARATUS

The present application is the U.S. national phase of international application number PCT/SE01/00530, filed Mar. 14, 2001, which claims the benefit of U.S. Provisional Application No. 60/189,084, filed Mar. 14, 2000.

The present invention relates to an apparatus for optical surface analysis of a sample area on a sensor surface. The invention is particularly concerned with a two-dimensional imaging surface plasmon resonance (SPR) apparatus suitable for use in biological, biochemical, chemical and physical testing.

BACKGROUND OF THE INVENTION

There is an interest in surface sensitive techniques for quantifying molecular interactions. Properties that are of interest are e.g. concentration of free analyte in solution, surface concentration of molecules on sensor surface, reaction kinetics between interacting substances, affinity of said substances, allosteric effects or epitope mappings. Examples of interacting substances are antigen-antibody, protein-protein, receptor-ligand, DNA-DNA, DNA-RNA, peptides-proteins, carbohydrates-proteins, glycoproteins-proteins, etc.

There are many techniques that are suitable for this task, e.g. surface plasmon resonance (SPR), resonant mirror, grating couplers, interferometers, surface acoustic wave (SAW), Quartz Crystal Microbalance (QCM) etc. So far, SPR is the dominating technique.

Areas of application are e.g. measurement of concentration of substances in biological research, biochemistry research, chemical research, clinical diagnosis, food diagnostics, environmental measurements, etc. Kinetic measurements can be used to determine rate constants as $k_{on}$ and $k_{off}$. Affinity measurements can be used to determine equilibrium association ($K_A$) or dissociation ($K_D$) constant as well as avidity.

SPR is a well-known phenomenon that consists of a bond electromagnetic wave, due to oscillations of electrons at the interface of a plasma. The surface plasmon can only exist at an interface between said plasma (e.g. a metal) and a dielectricum. A change in the optical constants of the dielectricum will change the propagation constant of the surface plasmon. The surface plasmon can be excited by light if the propagation constant of the light parallel to the interface is equal to, or close to, the propagation constant of the surface plasmon. Normally one uses the Kretschmann configuration [1] where a thin metallic film is applied on a prism, having a higher refractive index than the measured sample. The surface plasmon is then evanescently excited under total internal reflection, i.e. at an incident angle, normal to the surface, larger than the critical angle. At a certain incident angle, the component of the wave vector parallel to the surface meets the real part of the complex wave vector for a surface plasmon, and hence the light will couple into the surface plasmon and propagate at the interface between said plasma and said dielectricum. The surface plasmon will reradiate into the prism, and for a certain thickness of said plasma a destructive interference occur, leading to zero or close to zero intensity of reflected light. For a smooth surface of said plasma, coupled light will be absorbed in said plasma and generate heat.

When molecules bind close to the interface (within the probe depth of the surface plasmon) the interaction can be detected by a shift in the resonance condition of the surface plasmon. This can be detected as a shift in a reflected light intensity.

The SPR sensor can be used in an imaging mode, also denoted microscopy. This was at first proposed by Yeatman in 1987 [2]. Other setups are proposed by Bengt Ivarsson EP958494A1: ANALYTICAL METHOD AND APPARATUS [3, 4], or GWC Instruments SPRimager [5]. The latter utilizes many wavelengths in a non-simultaneous manner.

The surface plasmon resonance (SPR) phenomenon was already described in 1959 [6] and SPR apparatuses for thin adlayer analysis have been thoroughly described since 1968 [1, 7]. SPR setups for biosensing were used for the first time in 1983 [8] and for imaging applications in 1987 [2, 9]. With imaging SPR, also denoted SPR microscopy, new applications arise, e.g., label free—real time—multi spot biochemical analyses [10, 11], which can increase the throughput tremendously. The pioneering work on imaging SPR was undertaken by Knoll et al., who investigated surfaces patterned with Langmuir-Blodgett films [12, 13]. They also investigated the physical aspects of the technique, including lateral resolution [14], and proposed different setups, e.g. the rotating grating coupler [15].

There are in principal three different ways to measure changes in the SPR propagation constant. First, by measuring the reflected intensity (reflectance) at a flank of the SPR dip at a certain wavelength and incident angle. Second, by measuring the intensity of the reflected light versus the angle of incident light (angular interrogation). Third, by measuring the intensity of reflected light for different wavelengths at a certain incident angle (wavelength interrogation).

For zero-dimensional SPR (measurement of a single spot) said angular or wavelength interrogation requires at least a one-dimensional (linear) detector to make an instant measurement of the position of an SPR dip. For one-dimensional SPR (measurement of a single line) said angular or wavelength interrogation requires at least a two-dimensional (matrix) detector to make an instant measurement of the position of an SPR dip. In this case one dimension is used for the length scale (real image) and one dimension is used for the dip (either angle or wavelength). If two-dimensional SPR-measurement is performed, normally a dip cannot be resolved, i.e. one can normally only make an intensity measurement with a two-dimensional detector, i.e. for the two length scales. This means that only a limited portion of the dynamic range (effective refractive index of the sample) can be measured, due to the limited extension of the SPR-dips (in either angel or wavelength). Only at a small range will the slope of the SPR-dip be high, which means that there will be a limited range of high sensitivity.

To overcome these drawbacks the present invention provides a two-dimensional imaging surface plasmon resonance apparatus wherein a set of wavelengths can simultaneously (or pseudo-simultaneously) be used, e.g. by using a multi-wavelength light source and a color camera.

SHORT DESCRIPTION OF THE INVENTION

A new multi-wavelength surface plasmon resonance (SPR) apparatus for imaging applications is presented. It can be used for biosensing, e.g., for monitoring of chemical and biological reactions in real time with label free molecules. A set-up with a fixed incident angle in the Kretschmann configuration with gold as the supporting metal is described, both theoretically and experimentally. Simulations of the sensor response based on independently recorded optical (ellipsometric) data of gold show that the sensitivity for 3-dimensional recognition layers (bulk) increases with increasing wavelength. For 2-dimensional recognition layers (adlayer) maximum sensitivity is obtained within a limited wavelength range. In this situation, the rejection of bulk disturbances, e.g. emanating from temperature variations, decreases with increasing wavelength. For SPR imaging, the spatial resolution decreases with increasing wavelength. Hence, there is always a compromise between spatial resolution, bulk disturbance rejection and sensitivity. Most importantly, by simultaneously using multiple wavelengths, it is possible to maintain a high sensitivity and accuracy over a large dynamic range. Furthermore, our simulations show that the sensitivity is independent of the refractive index of the prism.

The main advantages of the invention are:
Improvement of the performance of imaging surface plasmon resonance (SPR).

By simultaneously using two or more wavelengths, both sides of the SPR-dip can be tracked, and hence dip width and dip depth changes can be detected. This will enhance both the accuracy and precision of the measurement. Absorbing substances (e.g. colloid gold) will induce dip width and dip depth changes.

By simultaneously using two or more wavelengths the measuring range can be extended.

By simultaneously using two or more wavelengths a high sensitivity can be obtained for a larger measuring range.

By using two or more wavelengths, different points on the sensor surface with different effective refractive indices can be measured simultaneously with a high sensitivity, high accuracy, and a high precision.

The simultaneous use of two or more wavelengths will not only improve sensitivity, accuracy, and precision, but will also improve the speed of analysis, i.e. a higher throughput is obtainable.

SHORT DESCRIPTION OF THE DRAWINGS

Figure 1A:
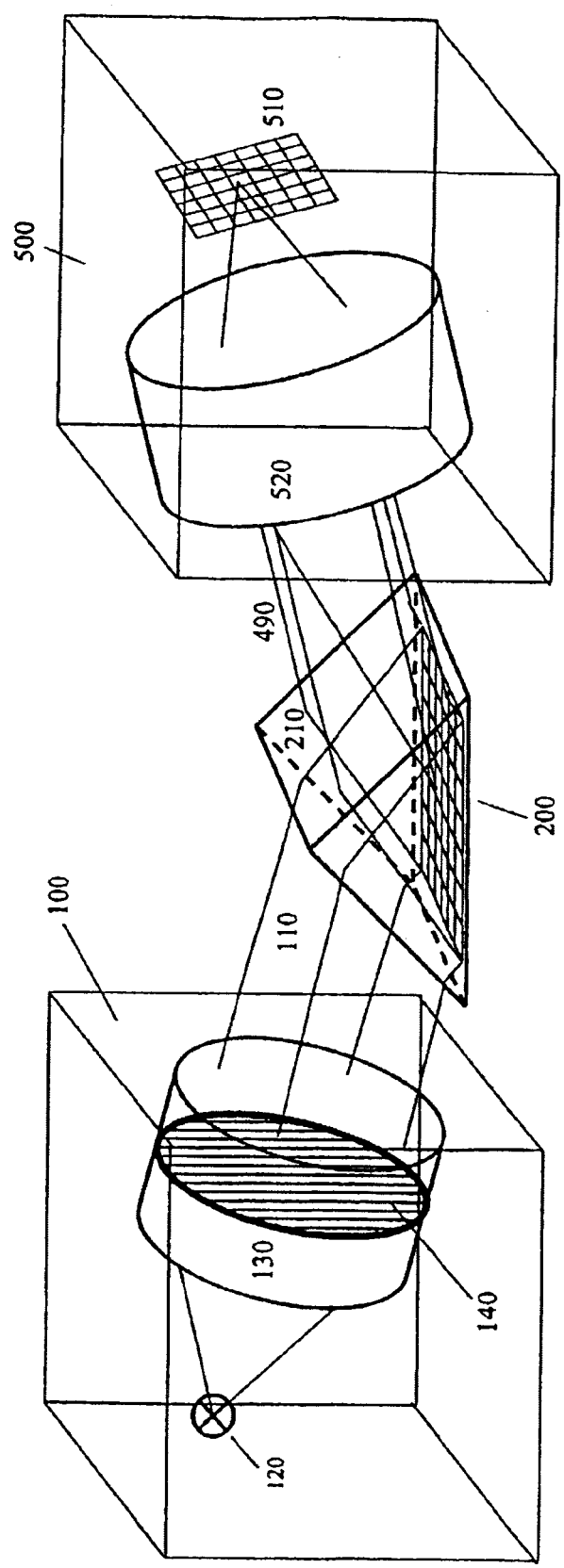
FIG. 1a is a multi-wavelength imaging SPR setup. The parameters are explained in the text.

FIGS. 16a–c shows reflectance images for an experimental setup at an incident angle of 68° and wavelengths 634, 692 and 751 nm, with gold as sensor metal layer and water as dielectricum.

The invention is now illustrated by description of embodiments with reference to the drawings and experiments, but it should be understood that the invention is not limited to the specifically disclosed embodiments.

DETAILED DESCRIPTION OF THE INVENTION

The present invention provides a two-dimensional imaging surface plasmon resonance apparatus which comprises a sensor surface layer of a conductive material that can support a surface plasmon, a source of electromagnetic beams of two or more wavelengths that illuminate a two-dimensional surface area from either the front or the backside of the sensor surface layer, and a detector for simultaneous, or pseudo simultaneous, detection of two or more wavelengths of reflected intensities from the two-dimensional surface area, providing two or more two-dimensional images of the surface area, the two-dimensional images being a function of the effective refractive index at each point on the surface area.

In an embodiment of the apparatus of the invention the conductive material is a free electron metal, such as gold, silver or aluminum. The sensor surface layer may be a grating.

In a preferred embodiment of the invention a prism is provided as a support for the sensor surface layer. The sensor surface layer may be supported on a planar transparent substrate plate, such as glass and plastics, optically attached to the prism, preferably by an index matching fluid, gel or glue.

The light source used in the apparatus of the invention may be selected from the group consisting of a) one or more monochromatic light sources, such as light emitting diodes or lasers, b) a glowing filament lamp, such as a Tungsten lamp, and c) a charge discharge lamp, such as a Xenon or Mercury lamp.

In an embodiment of the invention, the light from the light source is coupled into the sensor surface layer by a lens, fiber optics, or a mirror.

In another embodiment the light source provides a variable incident angle.

In yet another embodiment the light from the light source is collimated.

In still another embodiment the light of different wavelengths from the light source are impinging on the sensor layer, and by a rotating filter, pseudo-simultaneous impinging on the detector, which is synchronized to said rotating filter. The rotating filter can be placed anywhere in the optical path between the light source and the photo detector, i.e. before and after the sensor surface.

The detector used in the apparatus of the invention may be selected from the group consisting of a two dimensional array camera, charge coupled device (CCD), charge injection device (CID), photo diode array detector (PDA), photomultiplier and a CMOS sensor.

In an embodiment of the invention the detector has a mosaic filter.

In another embodiment two or more detectors are provided, and these are fitted with beam splitters and filters, such as interference filters, to enable measurement of different spectral properties.

In yet another embodiment the filter(s) is(are) adjustable.

In still another embodiment the detector(s) is(are) connected via an optical fiber bundle.

In a preferred embodiment the detector is a photographic film.

The apparatus of the invention may have a lens system, such as fixed focal length or a zoom, to magnify or reduce the image.

In a most preferred embodiment the apparatus operates with wavelengths at or close to the highest slope of the dip, either reflectance versus wavelength or reflectance versus the effective refractive index seen by the surface plasmon.

In a further embodiment of the invention, the light that hits the detector is p-polarized by a polarizer.

In another preferred embodiment the two-dimensional images put together result in a color image.

The invention will now be described with reference to the drawings.

FIG. 1a illustrates one embodiment of the apparatus of the invention wherein a collimated input beam 110 emanates from an illumination system 100 onto a sensor unit 200, preferably a prism (equilateral, right angle, hemispherical or aspherical) 210. The reflected light from said sensor unit is projected on an imaging system 500.

Figure 1B:
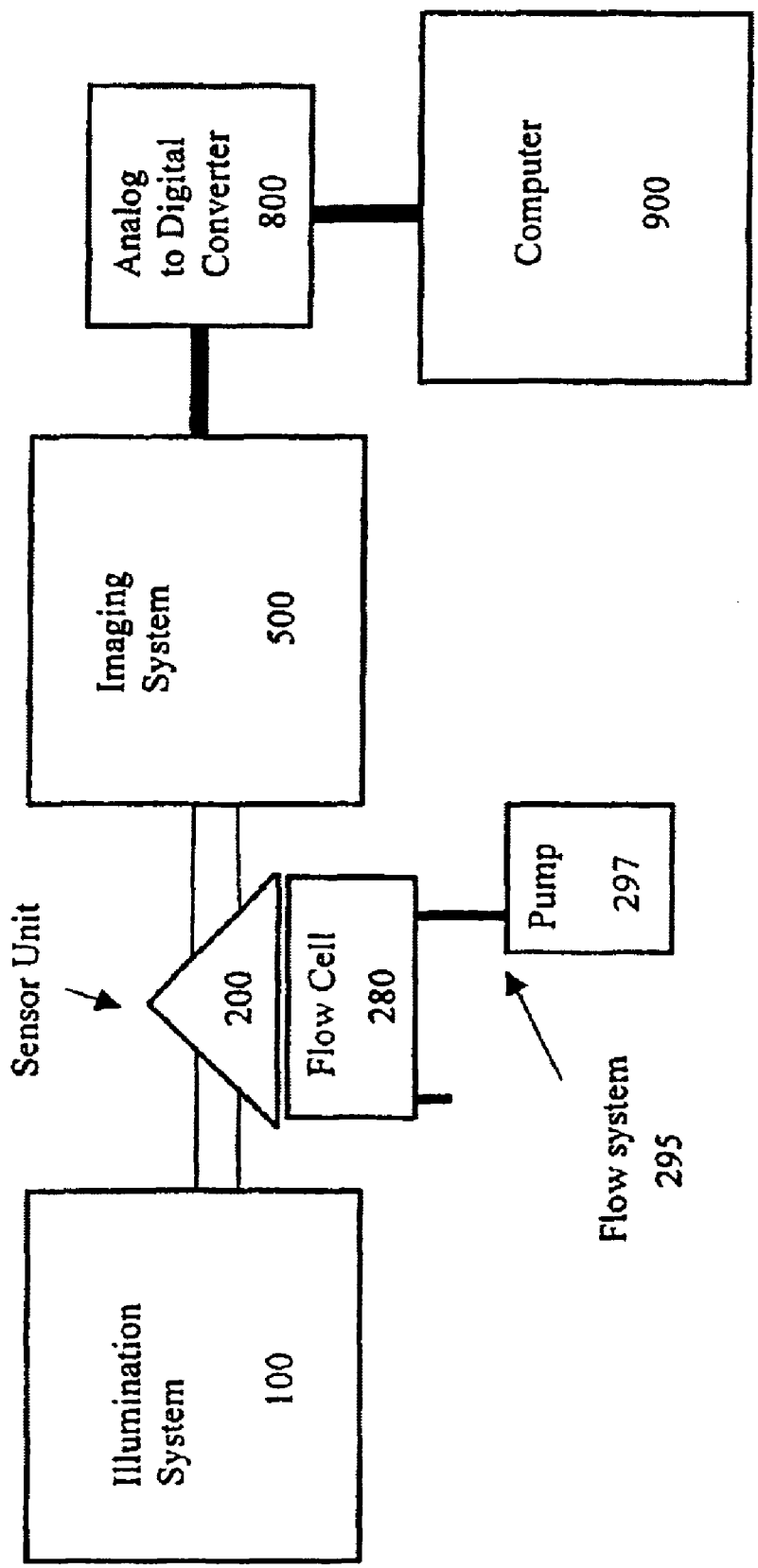
FIG. 1b shows schematically the apparatus with analog to digital converter and computer, and a flow cell with corresponding flow system (pump etc).

FIG. 1b illustrates schematically an apparatus of the invention with a computer 900 and an analog to digital converter 800 connected to the imaging system 500.

Figure 2A:
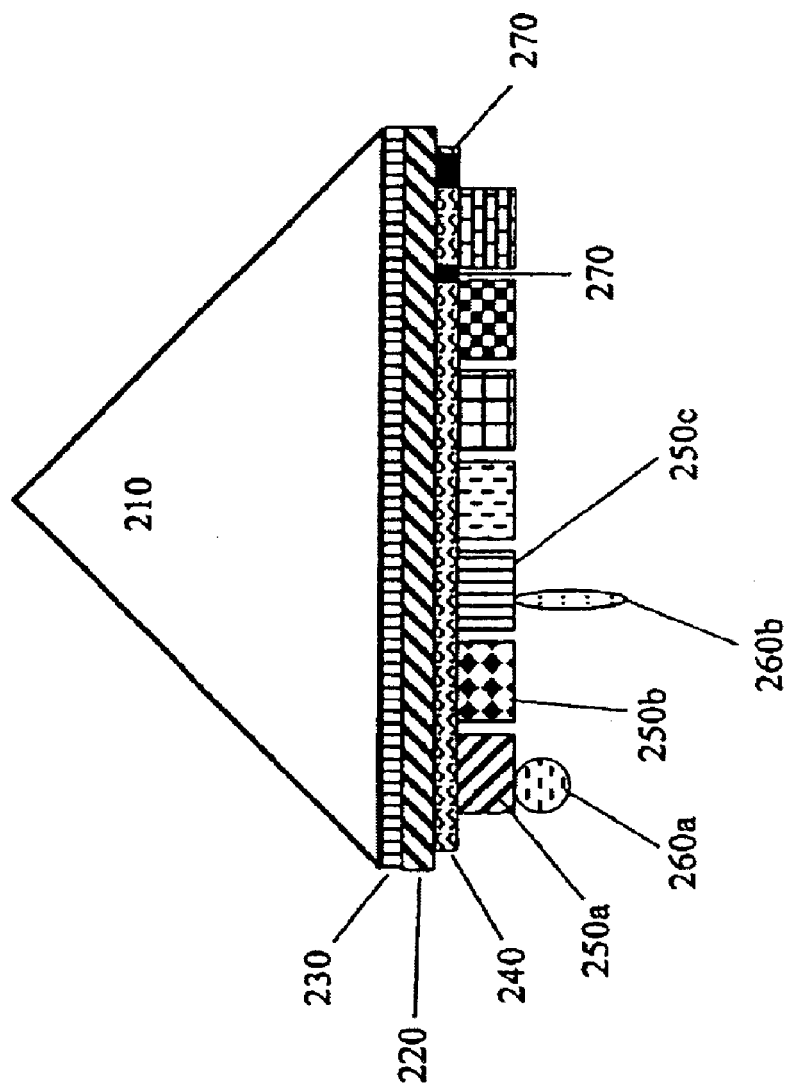
FIG. 2a shows the sensing unit in Kretschmann (back side illumination) configuration containing a prism, metal film and surface chemistry.

FIG. 2a shows the prism 210 of FIG. 1a onto which a metal film 220 has been evaporated (thermally or by sputtering). The prism 210 is transparent (glass or a polymer). A glass prism can be made of high refractive index e.g. flint glass or standard glass e.g. crown glass. A polymer prism can be made of non-crystalline plastics like polymethylmethacrylate, polycarbonate, styrene, SAN, glycol modified PET, etc. The metal film sensor is preferable gold if high chemical resistance is wanted. The metal film sensor can be silver if high sensitivity is preferred, but chemical resistance is not critical. The metal film is preferably evaporated on an evaporated (thermally or sputtered) adhesion layer 230. The adhesion layer 230 is preferably chromium or titanium. The adhesion layer is typically 0.5 nm thick. The adhesion layer is normally not a totally covering film due to the limited thickness. A too thick adhesion layer will lower the sensitivity of the apparatus. The thickness of said gold film is typically 45 to 50 nm. The thickness of said silver film is typically 56 nm. The metal layer 220 may have the form of a pattern. The pattern can be made by reactive etching using a photo lithography process. The metal layer may be covered by a linker layer 240. The linker layer can be an alkane thiol. The alkane thiol may function as a handle to specific molecules 250a, 250b, etc. The attached specific molecules can have an affinity to other species 260a, 260b, etc. The linker layer 240 can be in the form of a pattern. The metal film can be provided with a pattern by use of an inert film 270. The inert film can be photosensitive benzocyclobutenes (photo-BCB).

Figure 2B:
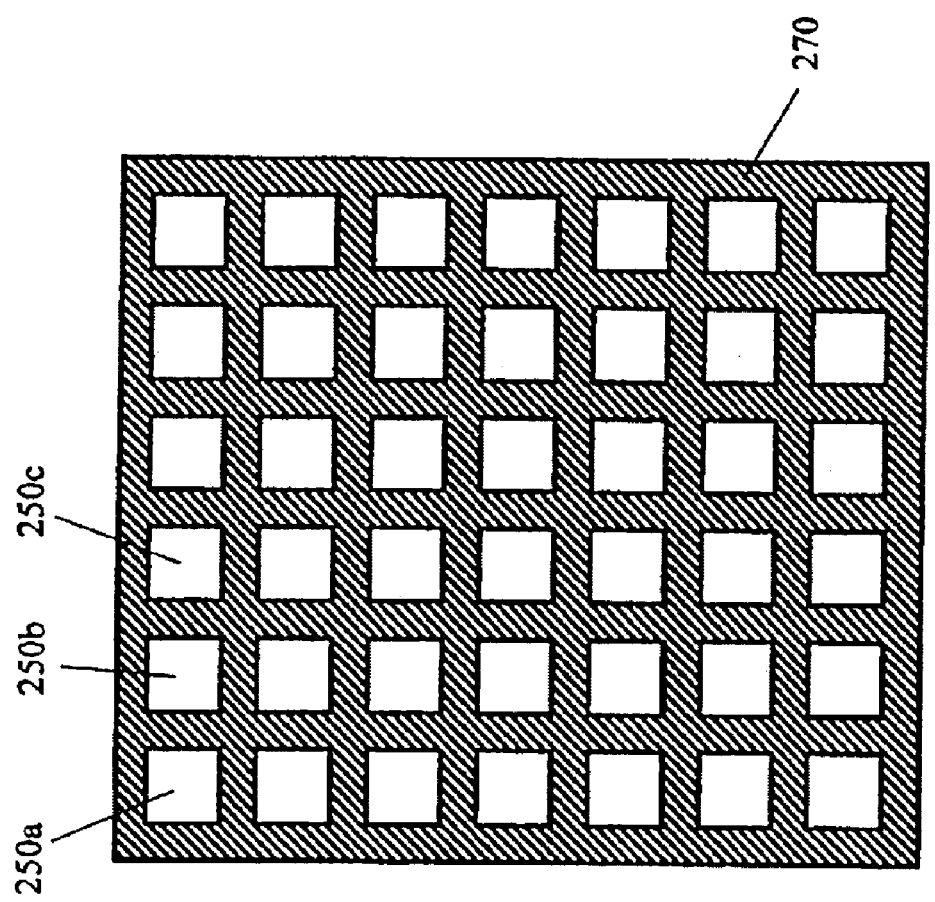
FIG. 2b shows a patterned sensor surface, with 6×7=42 measuring spots.
Figure 2C:
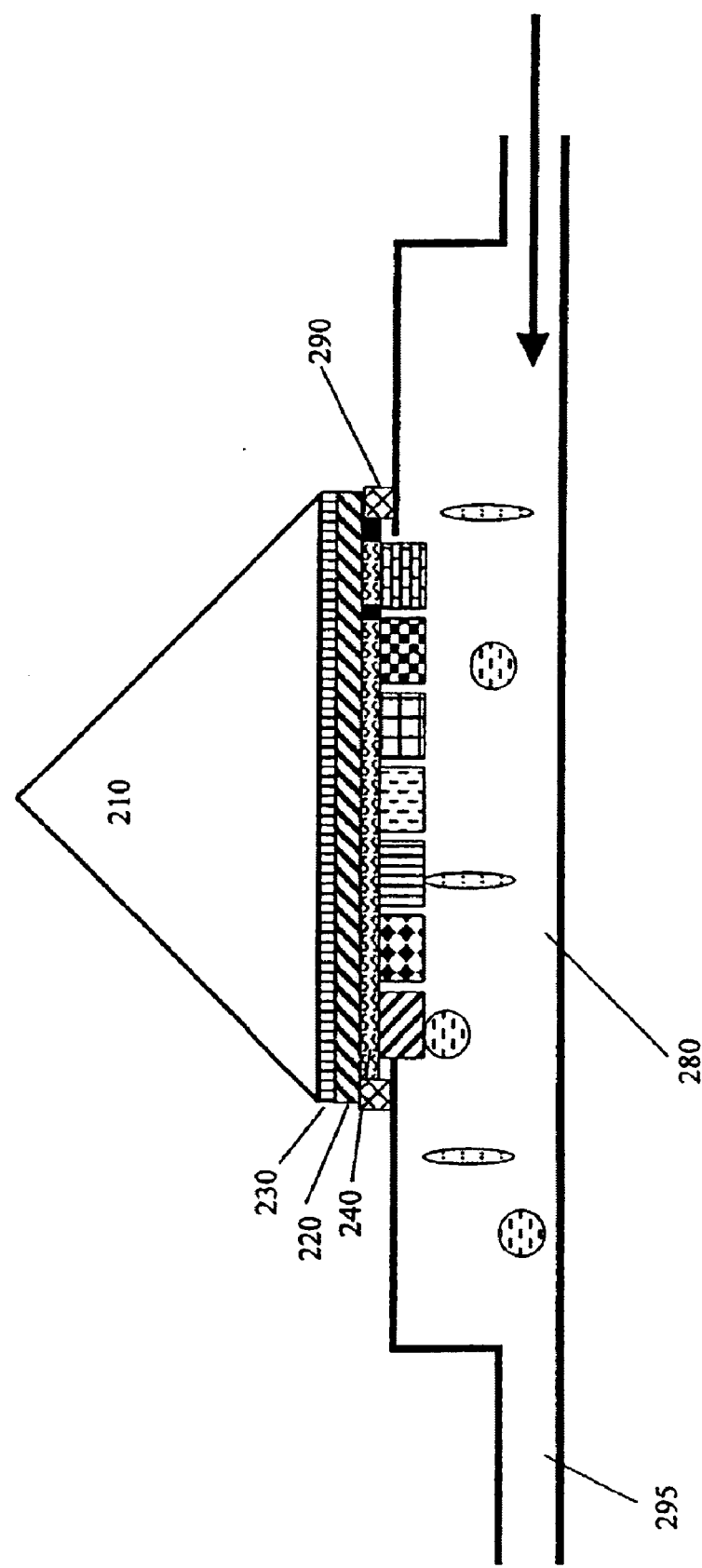
FIG. 2c shows a flow cell attached to the sensing unit.
Figure 2D:
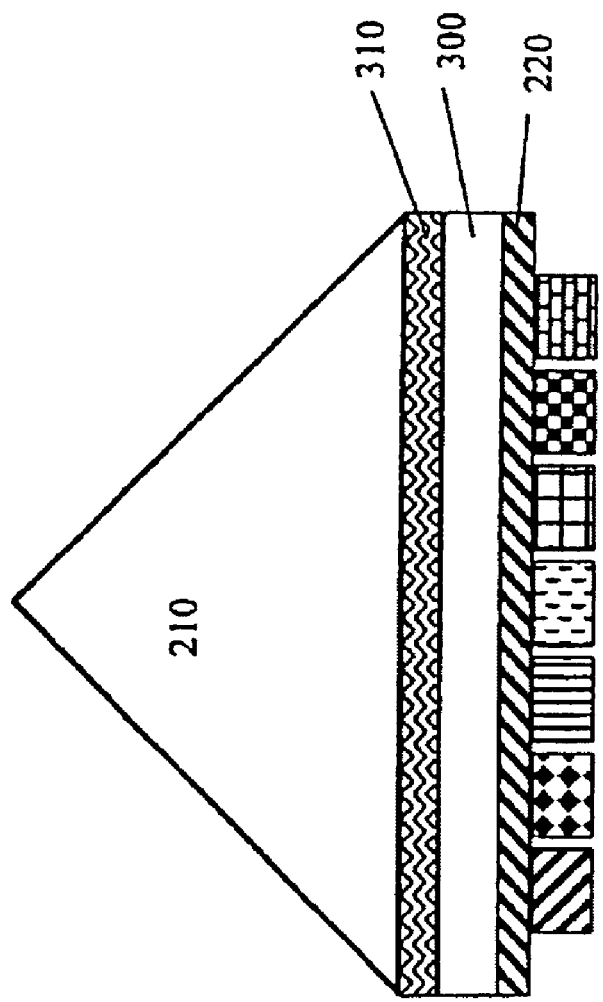
FIG. 2d shows a version with exchangeable sensing chips.

FIG. 2b shows the base of the prism 210, or transparent substrate 300 (FIG. 2d).

FIG. 2c shows the prism 210 onto which a flow cell 280 has be attached. To avoid leakage, a seal 290 can be inserted between the prism 210 and the flow cell 280. The flow cell can be made of a plastic material (polymethylmethacrylate, polycarbonate, styrene, polyvinylchloride, polyetheretherketone, polyamide etc.). The flow cell can be fitted to a flow system 295. The flow system may comprise a pump 297 (e.g. syringe pump or peristaltic pump), valves and tubing, as illustrated in FIG. 1b.

FIG. 2d shows the prism 210 with a metal film 220 evaporated on a transparent substrate 300. The substrate may be a plastic material, glass or semiconductor. The substrate 300 has preferably the same or similar optical constants as the prism 210. To obtain good optical contact between said prism and said transparent substrate, an optical interface 310 is used. The optical interface 310 should have optical constants equal to or close to those of said prism and said transparent substrate. The optical interface may be an index matching fluid, a gel, or a glue.

Figure 3:
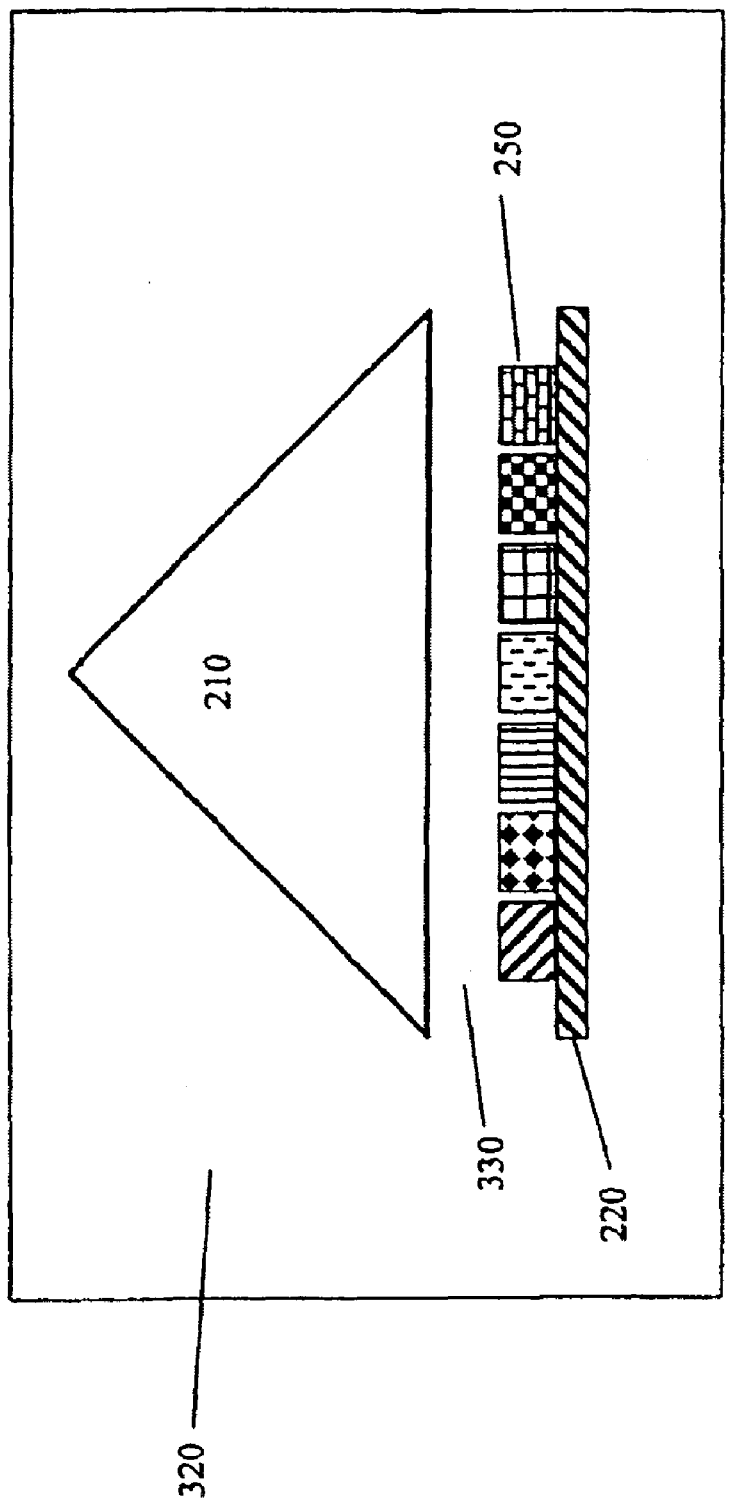
FIG. 3 shows a sensing unit in the Otto configuration (front side illumination)

FIG. 3 shows an optical system denoted Otto configuration 320. Said Otto configuration utilizes an air or liquid gap 330 to evanescently excite the surface plasmon.

Figure 4:
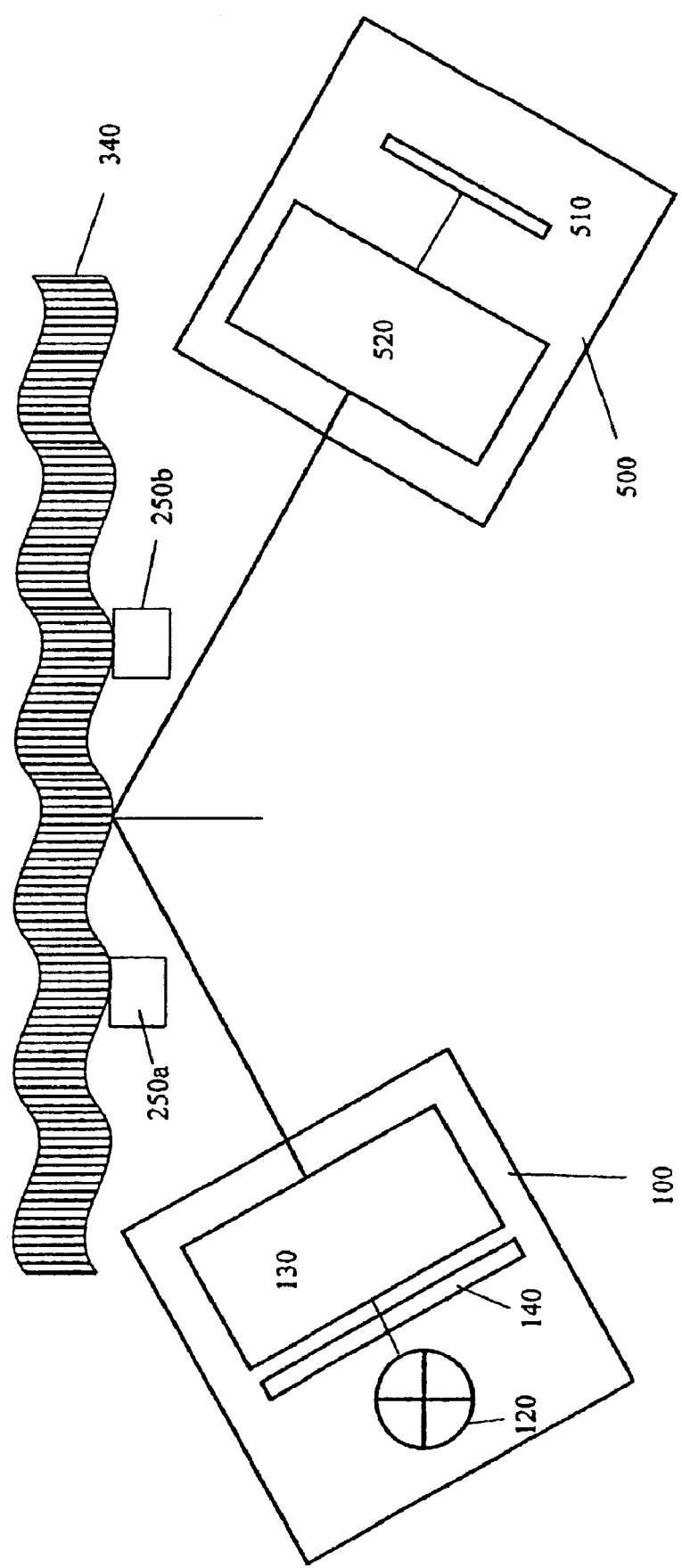
FIG. 4 shows an instrument with grating coupling

FIG. 4 illustrates a setup wherein the multi wavelength SPR can be excited by a corrugated metal film (grating) 340. In this case the metal film sensor does not need to be thin.

Referring to FIG. 1a, the illumination system 100 comprises a light source 120. Said light source can be a glowing filament, e.g. a tungsten-halogen lamp, or an arc discharge lamp, e.g. Xenon lamp, or lasers, e.g. diode lasers, dye lasers etc, or light emitting diodes (LEDs). Radiation from said light source is collected by a lens system 130, which creates a collimated (parallel) light beam 110. The lens system 130 can be a positive lens, e.g. f=150 mm, or a condenser system, or a more sophisticated lens system. At some point in the beam of said illumination system a polarizer can be inserted 140. Said polarizer can be a dichroic sheet, Glan-Thompson polarizing prisms, Glan-Taylor polarizing prism or Wollaston prisms. The polarizer or polarizing equipment shall transmit light parallel to the plane of incidence (p-polarized or transverse magnetic, TM). The use of a polarizer will improve performance, but is not necessary. A surface plasmon can only be excited by p-polarized light, hence light polarized transverse the plane of incidence (s-polarized or transverse electric, TE) will be reflected at the sensor surface. Absence of a polarizer will hence decrease the depth of the SPR dip, which may be a disadvantage, due to non-informative signal added to the informative SPR signal at the imaging system 500.

The imaging system 500 utilizes at least one area detector 510, which can be a photographic film, e.g. a color film (negative or dia positive), an electronic photo device, e.g. photo diode array, charge coupled device (CCD), charge injection device (CID), CMOS array etc. The area detector 510 may be a color device. The color device may include a mosaic color filter.

Figure 5:
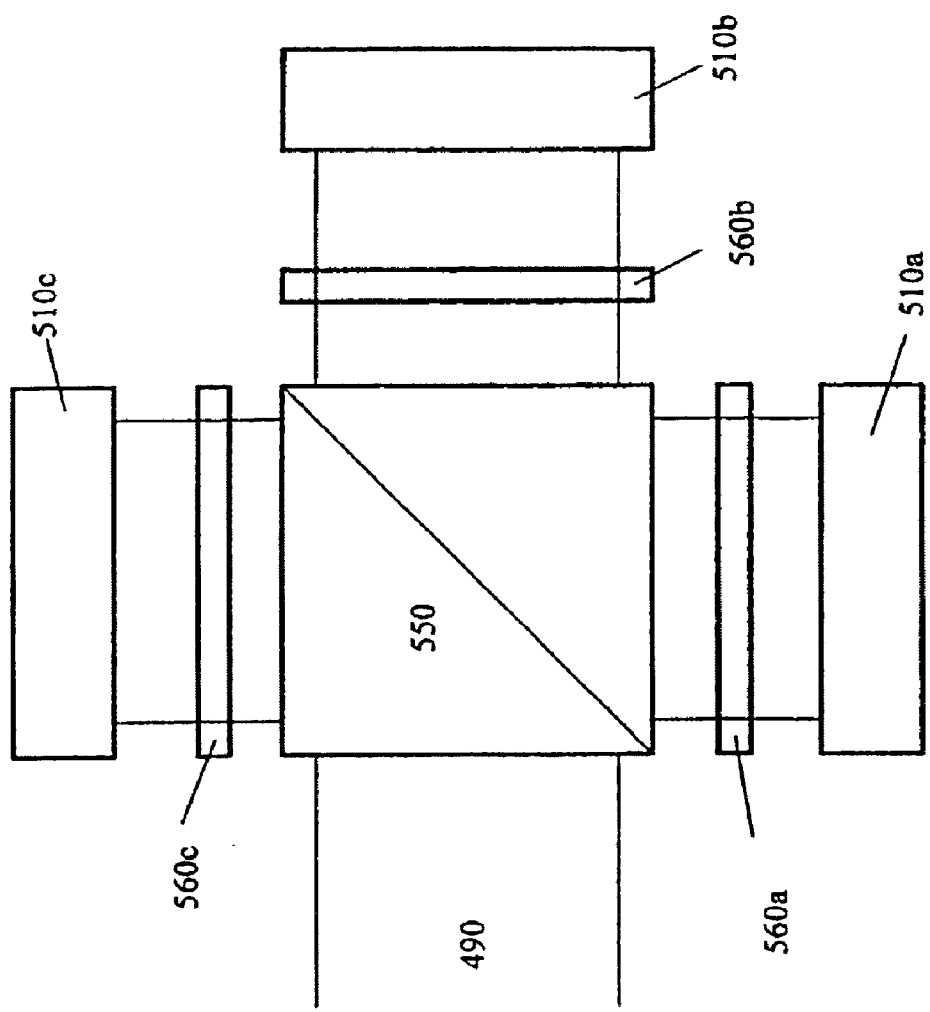
FIG. 5 shows a multi-detector arrangement.

FIG. 5 illustrates an imaging system 500 that consists of more than one area detector 510a, 510b, 510c, one for each wavelength. In this case, a reflected light beam 490 is divided by beam splitters 550 and color filters 560a, 560b, 560c, in the same way as used in commercial 3 CCD video cameras. The color filters can either be narrow and non-overlapping in wavelength, or be broad with overlapping wavelengths.

Figure 6:
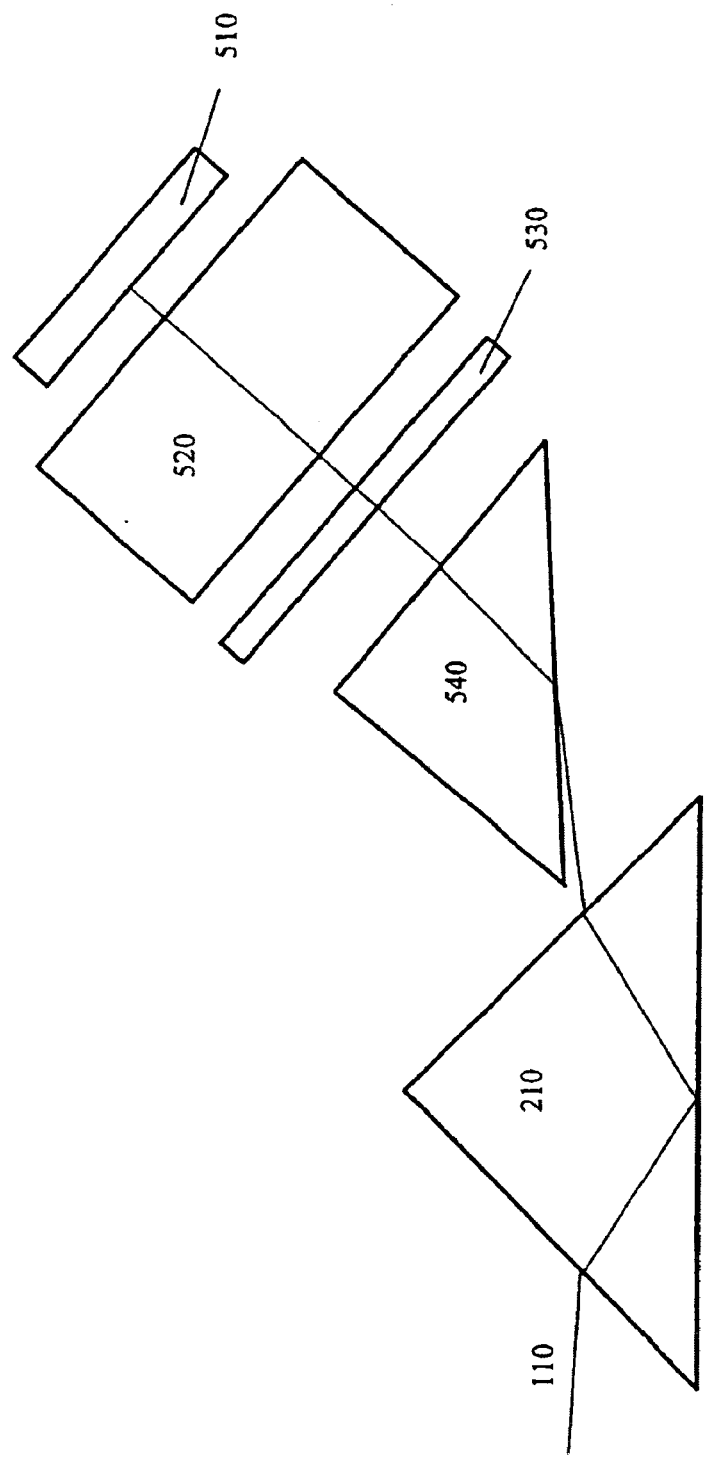
FIG. 6 shows an imaging system.

FIG. 6 illustrates a setup for improving image quality by use of an imaging lens 520. The imaging lens 520 can be an ordinary focusing camera lens, and it can be further improved by adding a cylindrical lens 530. Image restitution is possible by adding a secondary prism 540, cylinder lens or by tilting the area detector.

Figure 7:
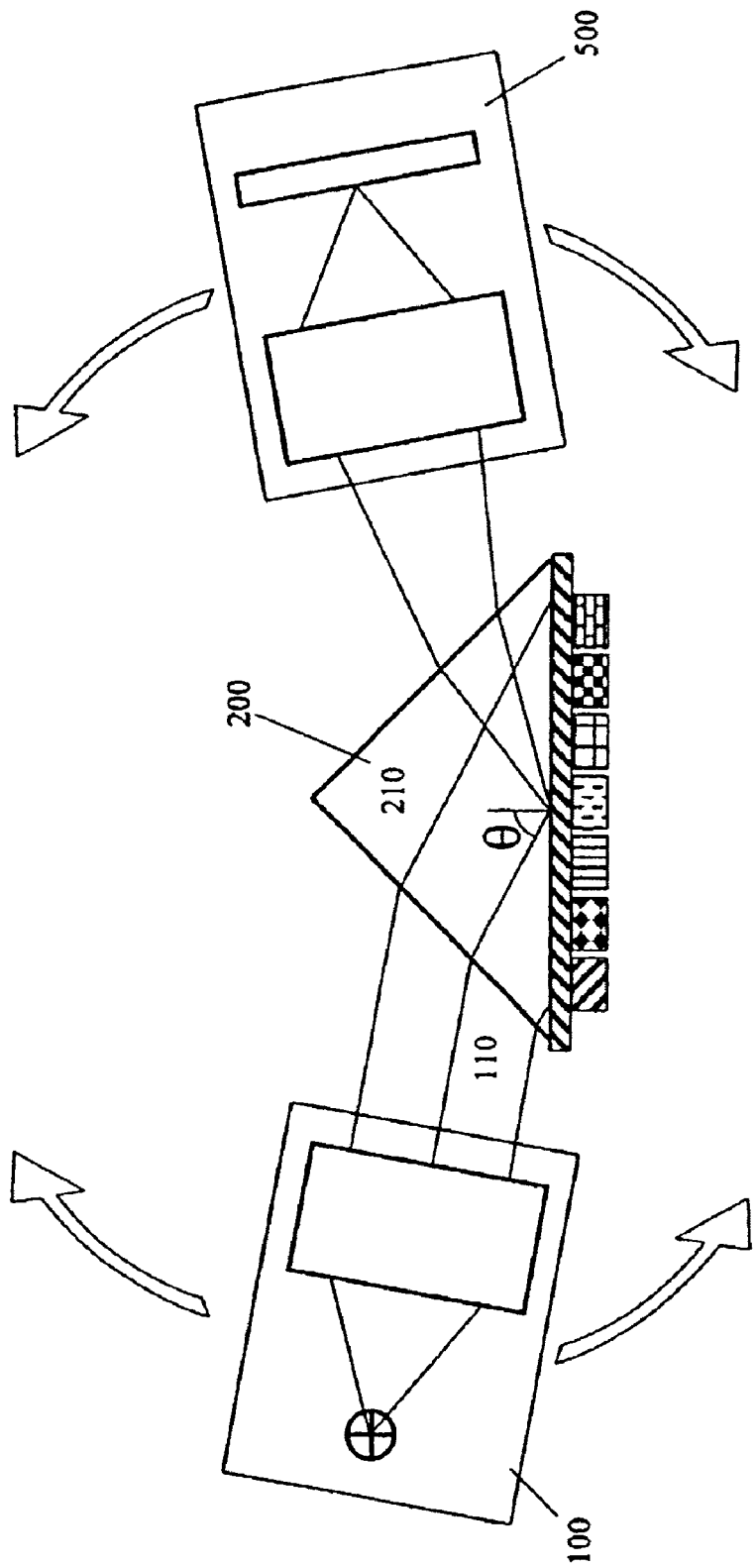
FIG. 7 shows that it is possible to change incident angle.

FIG. 7 shows an embodiment wherein the incident angle of the light beam 110 can be altered by rotating the illumination system 100 with respect to the prism 210. The imaging system 500 is rotated by the same amount as the prism 210, but in the other direction. The rotation can be performed by a goniometer, i.e. a θ, 2θ system, where the illuminating system is fixed and the prism is rotated θ and the imaging system is rotated 2θ.

Figure 8A:
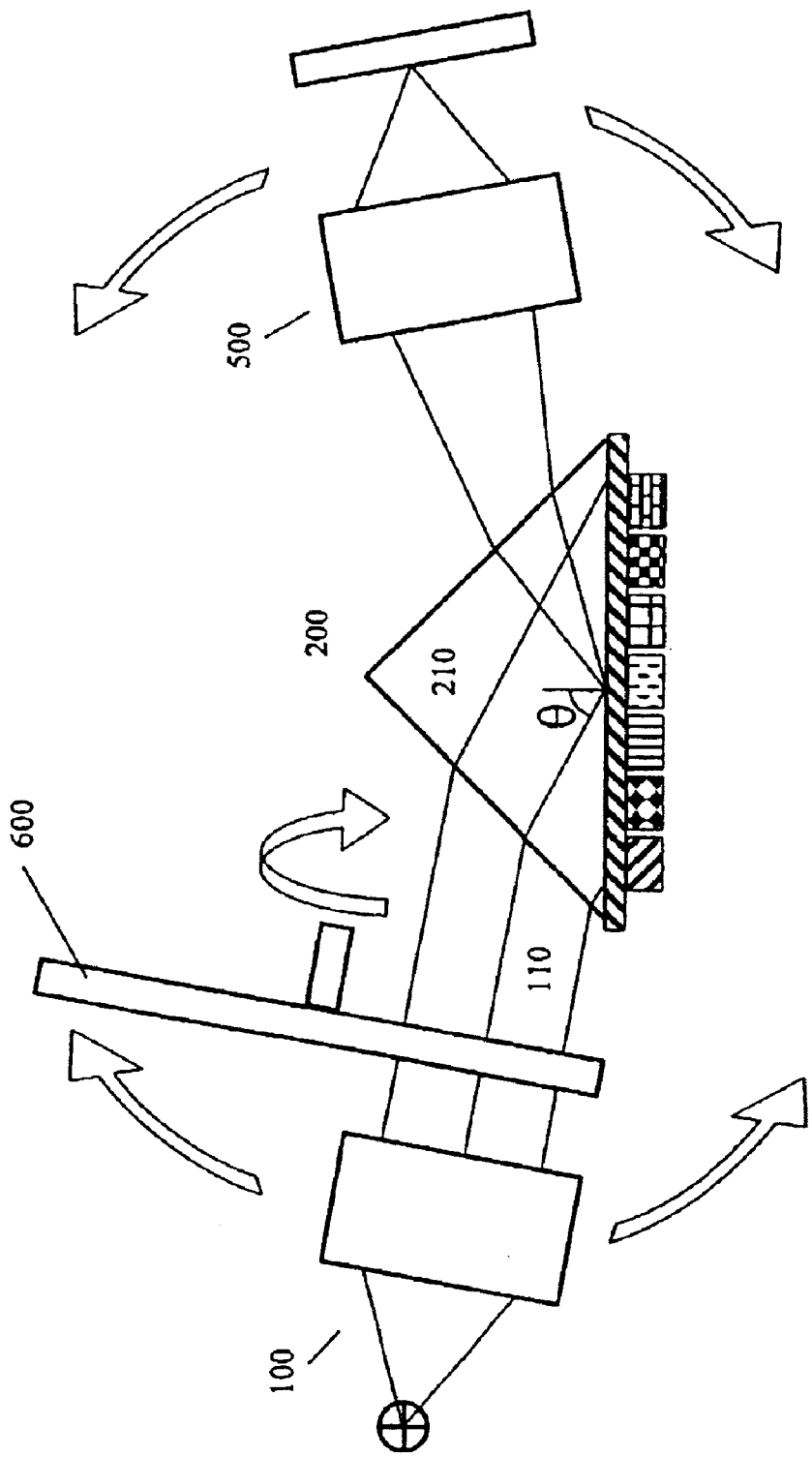
FIG. 8a shows a setup with interchangeable filters (pseudo simultaneously)
Figure 8B:
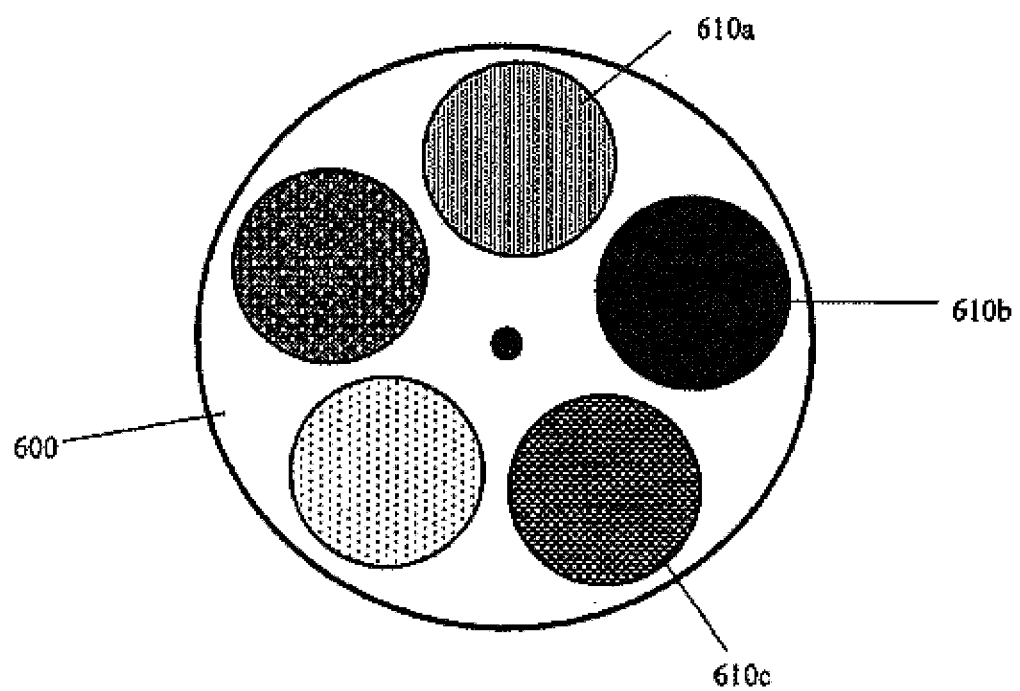
FIG. 8b shows a rotating filter wheel.

FIG. 8a shows an embodiment wherein the multi-wavelength feature described in relation to FIG. 7 can be fulfilled in a pseudo simultaneously manner with a filter device 600. The filter device 600 can be a rotating filter wheel as illustrated in FIG. 8b. The rotating filter 600 can be a band pass filter 610a, 610b, 610c, etc. Said band pass filter can be an interference filter. Another method to change wavelength is to use an electro-optical device, e.g. a Fabry-Perot cell. Change of filter is synchronized with the detector.

The two-dimensional imaging surface plasmon resonance apparatus of the invention can be oriented in any direction (vertical, horizontal or any angle between). The sensor surface can be faced upwards, downwards or any arbitrary direction in space.

DESCRIPTION OF EXPERIMENTS

It is shown how SPR imaging can be performed with a color camera. The camera allows simultaneous intensity measurements at different wavelengths, which will increase the dynamic range and increase the sensitivity and accuracy over a larger range of the refractive index of the sensing medium. The sensing medium can be a 3-dimensional bulk material or a 2-dimensional adlayer. For the latter, the thickness change can be monitored if the refractive indices of both the adlayer and the surrounding medium are known.

Figure 11:
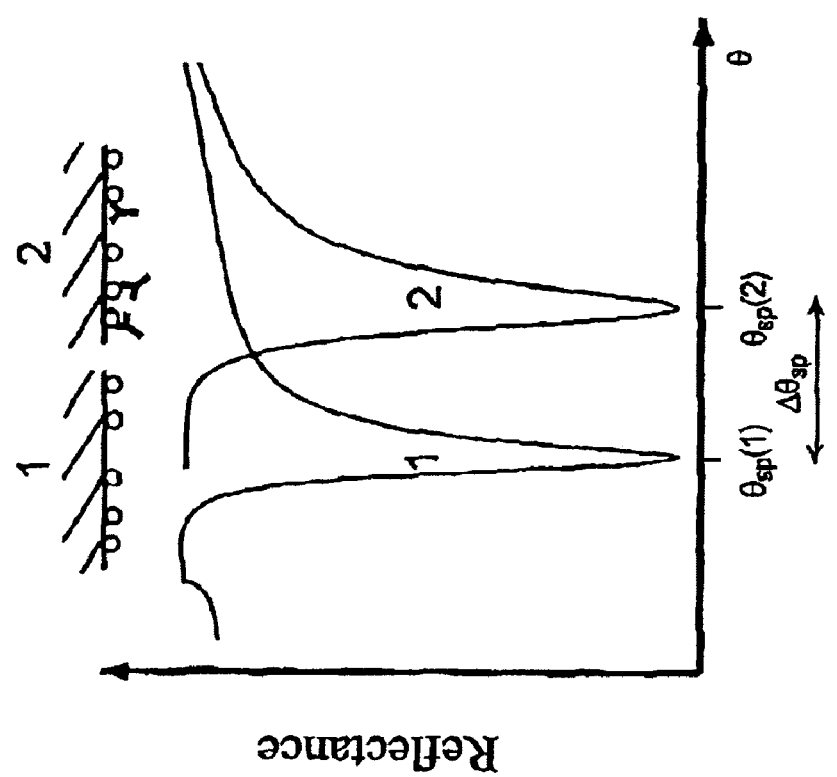
FIG. 11 shows an SPR-dip in angular interrogation.
Figure 12:
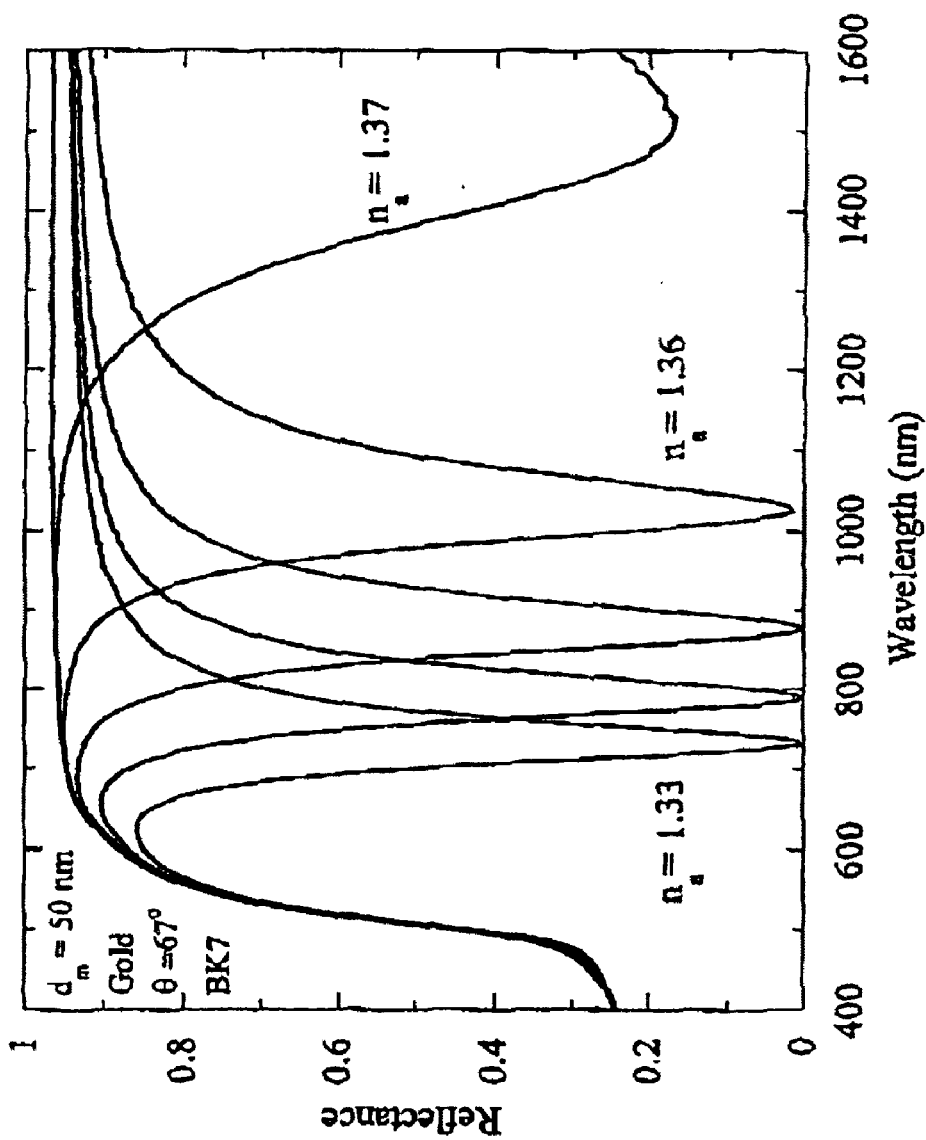
FIG. 12 shows an SPR-dip in wavelength interrogation.

For an SPR apparatus working in angular interrogation (FIG. 11, reflectance versus incident angle) simulations (with Fresnel equations) and measurements show that the resonance angle $\theta_{sp}$ increases $\Delta\theta_{sp}$ for increasing effective refractive index, e.g. by an adlayer formation (case 2 in FIG. 11). Case 1 in FIG. 11 is without an adlayer, i.e. a lower effective refractive index is seen by the sensor. Simulations (Fresnel equations) and measurements show that the resonance wavelength increases with increasing effective refractive index (e.g. adlayer formation) for an apparatus working in the wavelength interrogation (FIG. 12). The conditions used in the example is a gold film of thickness, $d_m$, equal to 50 nm, an incident angle, θ, equal to 67°, and a prism 210 made of BK7 glass. The curves in FIG. 12 illustrate the reflectance versus wavelength for effective refractive indices, $n_a$, from 1.33 to 1.37.

Figure 13:
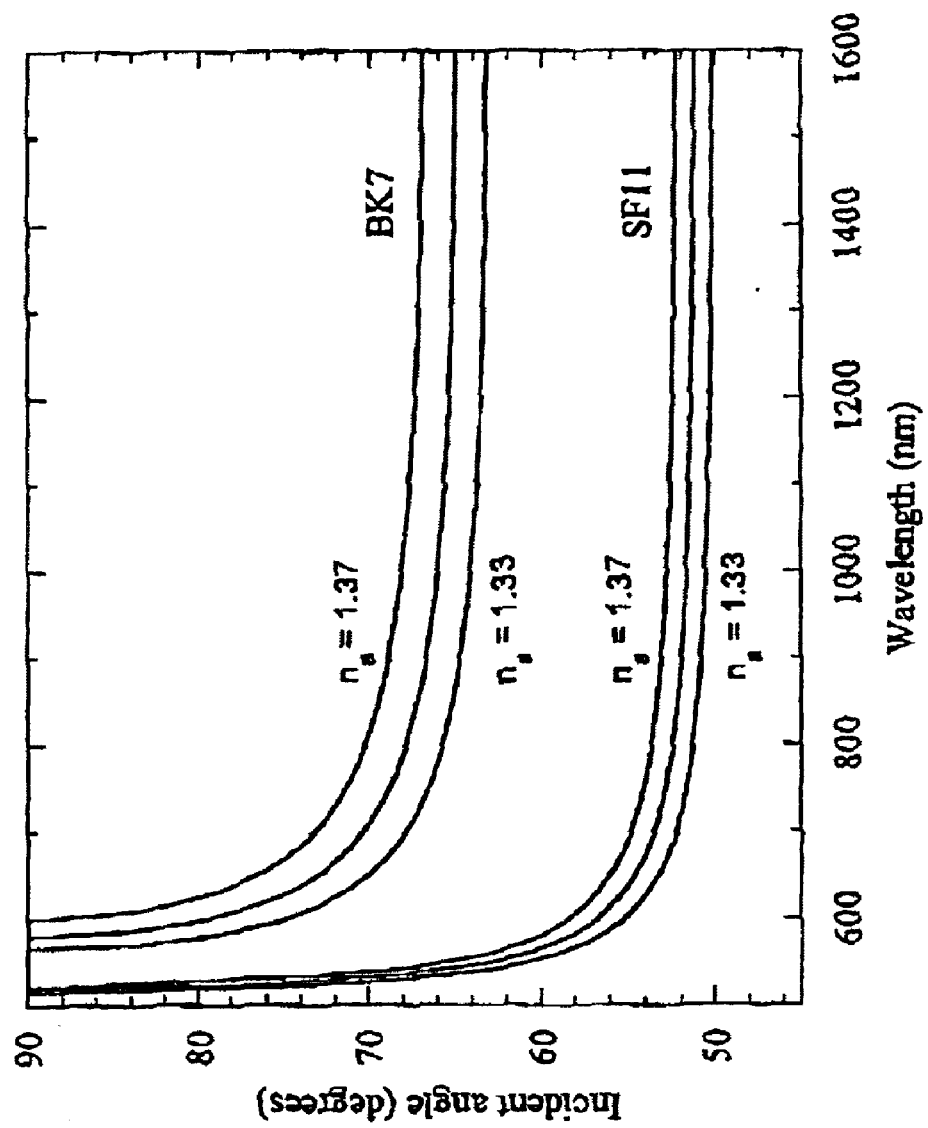
FIG. 13 shows the relationship between the incident angle for at the SPR condition and wavelength for gold (i.e. the dispersion relation). Two prism materials are shown, BK7 and SF11.
Figure 14:
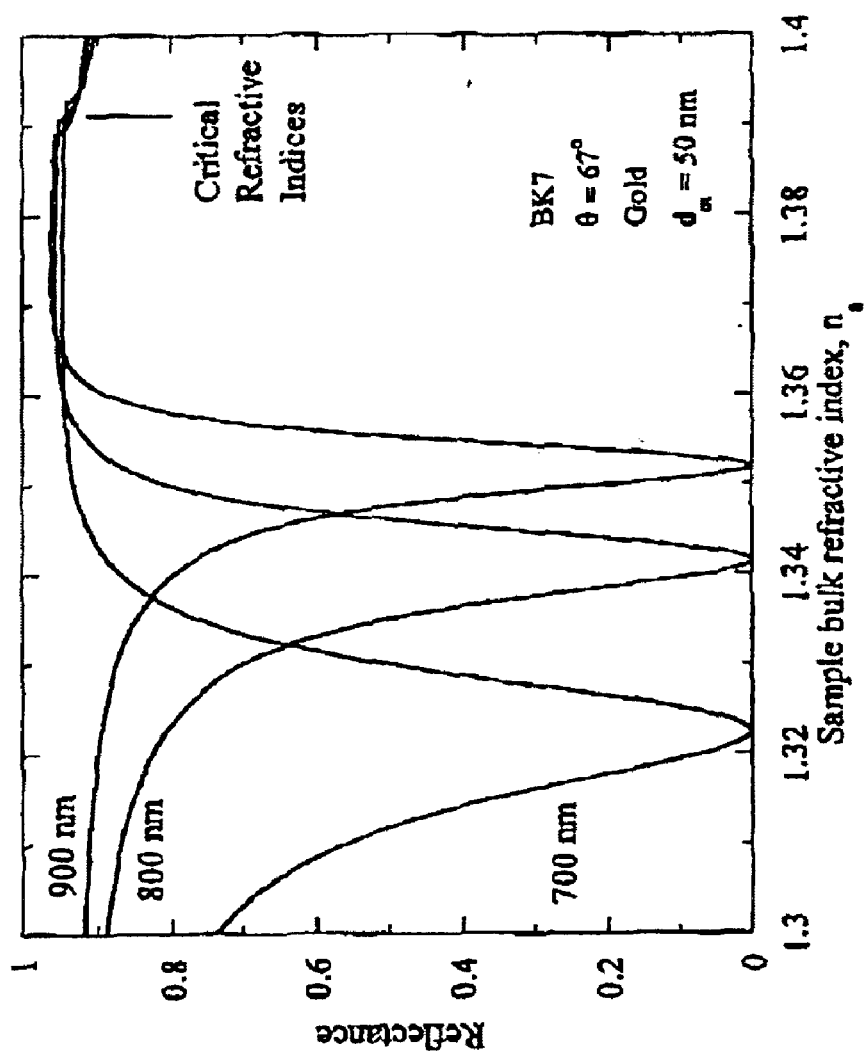
FIG. 14 shows the reflectance versus effective refractive index, at the sensor surface, for gold at three different wavelengths at an incident angle of 67 degrees.
Figure 15:
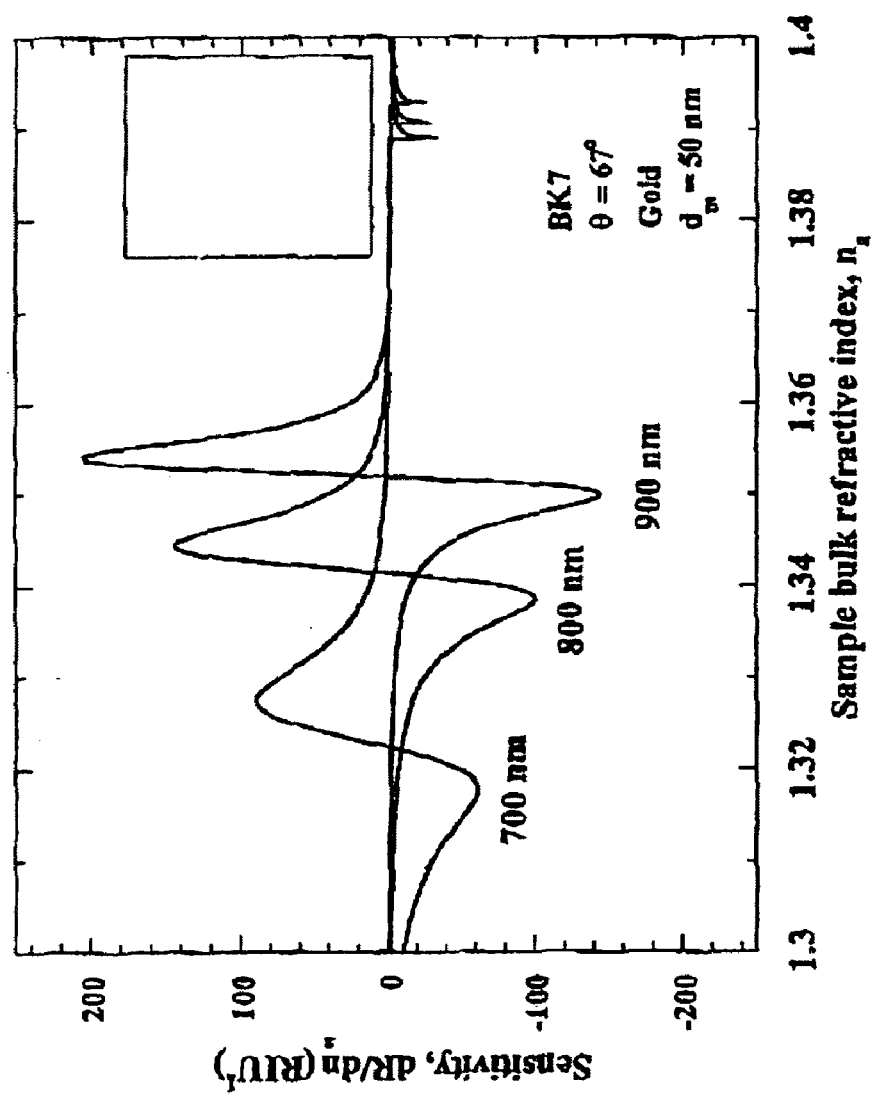
FIG. 15 shows the sensitivity versus effective refractive index, at the sensor surface, for gold at three different wavelengths at an incident angle of 67 degrees. The curves in FIG. 15 are the derivatives of the curves in FIG. 14.

Referring to FIG. 13 and Fresnel calculations, the SPR dip-valley (minimum reflection) will move in a right upward direction upon increasing effective refractive index, $n_a$, of the dielectricum, e.g. an adlayer formation. The curvature of the dip-valley is an effect of the SPR-dispersion relation emanating from the dispersion of the metal (i.e. change of dielectric constant as a function of wavelength). The incident angle, wavelength, refractive index of the prism 210 and effective refractive index of the sample for the SPR imaging equipment are coupled (due to the dispersion relation of the surface plasmon). Curves from two different setups are shown in FIG. 13, one corresponds to a prism 210 made of BK7 glass (refractive index approximately equal to 1.5), and the other corresponds to a prism 210 made of SF11 glass (refractive index approximately equal to 1.5). The incident angle is be plotted versus the refractive index of the sample (FIG. 14) for the same conditions as in FIG. 12, using three wavelengths (700, 800, and 900 nm). The incident angle and wavelength is preferably chosen so that the derivative (FIG. 15) of the reflectance versus effective refractive index (FIG. 14) is maximized. The derivatives of the reflectance versus effective refractive index for an example with a 50 nm gold film, at an incident angle of 67°, for three different wavelengths (700, 800, and 900 nm), and different effective refractive indices are shown in FIG. 15.

Figure 16:
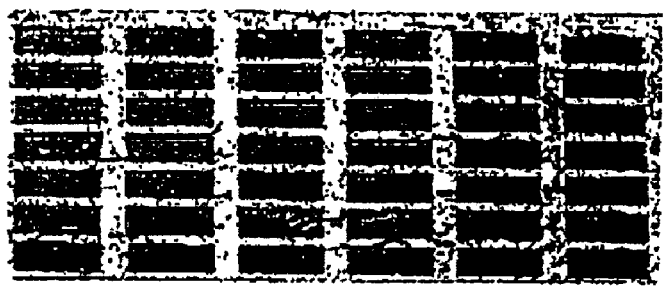
Figure 16:
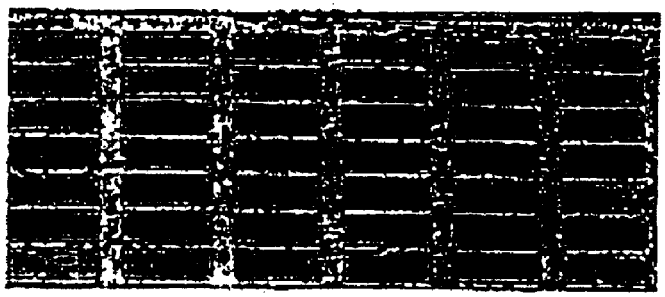
Figure 16:
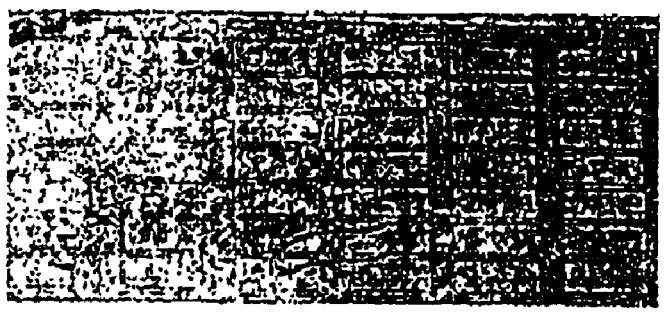

An example of a sensor surface that has individual sensor spots on a gold film 220 is shown in FIG. 16 for wavelengths 634, 692 and 751 nm, at an incident angle of 68° and a prism made of BK7 glass. The effective refractive index of the sample is approximately 1.33.

EXAMPLE 1

Figure 9:
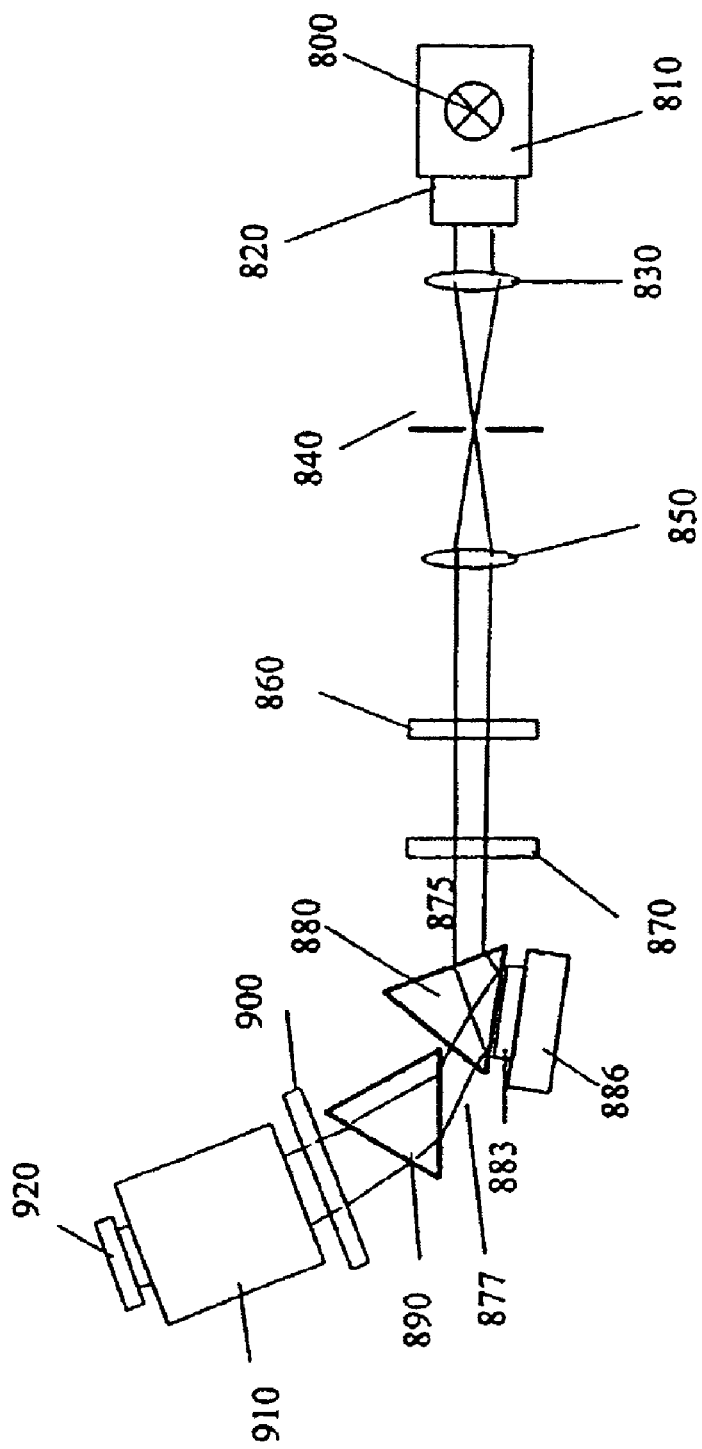
FIG. 9 shows an experimental setup with a sophisticated imaging system.

FIG. 9, which illustrates one embodiment of the two-dimensional imaging surface plasmon resonance apparatus of the invention, utilizes a white light source comprising a 300 W Xenon Arc lamp 800 (Oriel Inc., Stratford, Conn., USA), in a housing 810 (Oriel) containing a F/1 condensing lens assembly 820 (Oriel). Collimated light is focused by a positive lens, f=150 mm 830 (Oriel), onto a 400 m pinhole 840 (Melles Griot Inc.). A second lens, f=150 mm 850 (Melles Griot), creates a collimated light beam 875, which is filtered by a filter wheel 860 consisting of three interference filters of center wavelength 634, 692 and 751 nm respectively. All filters have a bandwidth of 10 nm. Said collimated beam is plane polarized by a dichroic sheet polarizer 870 (Melles Griot). The collimated light 875 impinges on an equilateral prism 880 made of BK7 glass (Melles Griot). Onto said prism is a glass substrate 883 attached by an index matching fluid (Cargille Inc.). The glass substrate contains the metal film supporting the surface plasmon resonance. The reflected light 877 from said prism 880 is directed to a right angle prism 890 made of BK7 glass (Melles Griot). Said prism 890 restitutes the image. A cylinder lens, f=100 mm, 900 is put between the said right angle prism 890 and a camera lens, Nikon micro f=60 mm, f/2.8, 910. The image from the sensor surface is projected on a CCD camera 920 (Orbis 2, Spectra Source Inc.)

EXAMPLE 2

Figure 10:
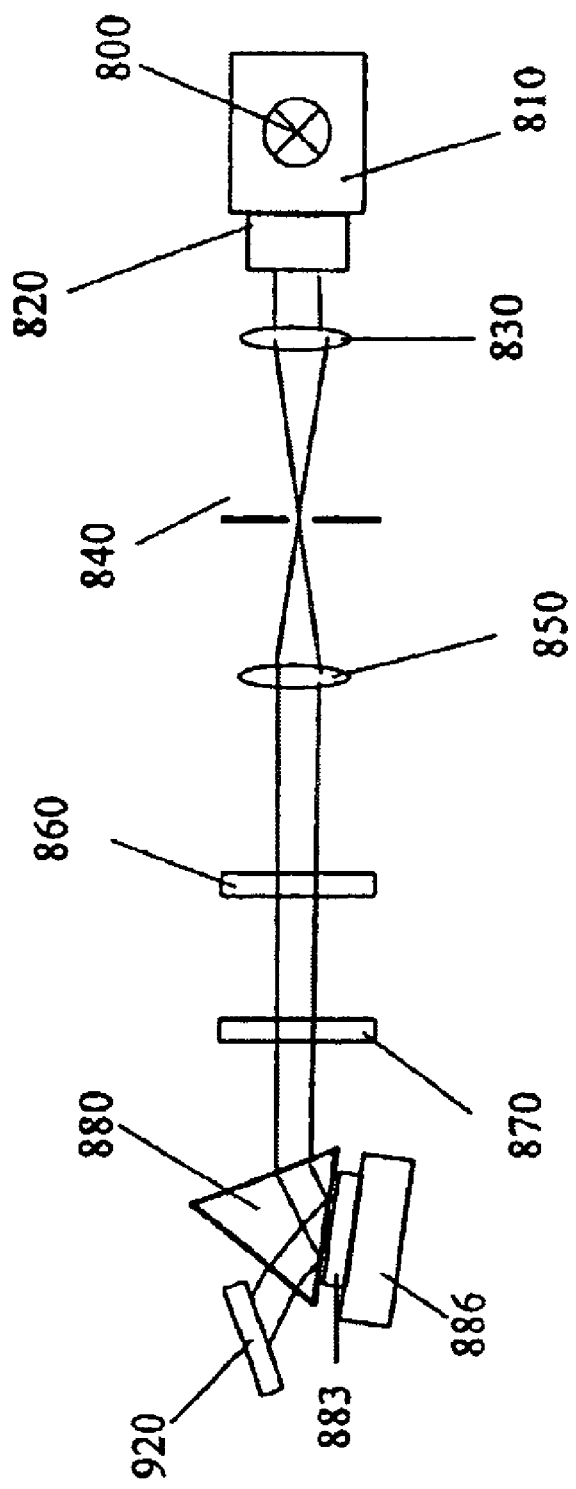
FIG. 10 shows an experimental setup with a simple imaging system.

FIG. 10, which illustrates another embodiment of the two-dimensional imaging surface plasmon resonance apparatus of the invention, utilizes a white light source comprising a 300 W Xenon Arc lamp 800 (Oriel Inc., Stratford, Conn., USA), in a housing 810 (Oriel) containing a F/1 condensing lens assembly 820 (Oriel). Collimated light is focused by a positive lens, f=150 mm 830 (Oriel), onto a 400 m p inhole 840 (Melles Griot Inc.), A second lens, f=150 mm 850 (Melles Griot), creates a collimated light beam 875, which is filtered by a filter wheel 860 consisting of three interference filters of center wavelength 634, 692 and 751 nm, respectively. All filters have a bandwidth of 10 nm. Said collimated beam is plane polarized by a dichroic sheet polarizer 870 (Melles Griot). The collimated light 875 impinges on an equilateral prism 880 made of BK7 glass (Melles Griot). Onto said prism is a glass substrate 883 attached by an index matching fluid (Cargille Inc.). The glass substrate contains the metal film supporting the surface plasmon resonance. The reflected light 877 from said prism 880 is projected on a CCD camera 920 (Orbis 2, Spectra Source Inc.) The camera is tilted to restitute the image.

All the references cited in this specification are included herein by reference.

REFERENCES

[1] E. Kretschmann, Die Bestimmung Optischer Konstanten von Metallen Durch Anregung von Oberflächenplasmaschwingungen, Z. Physik, Vol. 241, (1971), 313–324.

[2] E. Yeatman and E. Ash, Surface Plasmon Microscopy, *Electronics Letters*, Vol. 23, (1987), 1091–1092.

[3] B. Ivarsson, *Analytical Method and Apparatus*, Patent EP958494A1.

[4] B. Ivarsson, *Analytical method and apparatus*, Patent WO9834098A1.

[5] B. P. Nelson, A. G. Frutos, J. M. Brockman and R. M. Corn, Near-Infrared Surface Plasmon Resonance Measurements of Ultrathin Films. 1. Angle Shift and SPR Imaging Experiments, *Analytical Chemistry*, Vol. 71, (1999), 3928–3934.

[6] T. Turbadar, Complete Adsorption of Light by Thin Metal Films, *Proc. Phys. Soc. Lond.*, Vol. 73, (1959), 40–44.

[7] A. Otto, Excitation of Nonradiative Surface Plasma Waves In Silver by the Method of Frustrated Total Reflection, *Z. Physik*, Vol. 216, (1968), 398–410.

[8] B. Liedberg, C. Nylander and I. Lundström, Surface Plasmon Resonance For Gas Detection and Biosensing, *Sensors and Actuators*, Vol. 4, (1983), 299–304.

[9] E. M. Yeatman and E. A. Ash, Surface plasmon scanning microscopy, *Proceedings of SPIE*, Vol. 897, (1988), 100–107.

[10] C. E. Jordan and R. M. Corn, Surface Plasmon Resonance Imaging Measurements of Electrostatic Biopolymer Adsorption onto Chemically Modified Gold Surfaces, *Analytical Chemistry*, Vol. 69, (1997), 1449–1456.

[11] C. E. Jordan, A. G. Frutos, A. J. Thiel and R. M. Corn, Surface Plasmon Resonance Imaging Measurements of DNA Hybridization Adsorption and Streptavidin/DNA Multilayer Formation at Chemically Modified Gold Surfaces, *Analytical Chemistry*, Vol. 69, (1997), 4939–4947.

[12] B. Rothenhäusler and W. Knoll, Surface-plasmon microscopy, *Nature*, Vol. 332, (1988), 615–617.

[13] W. Hickel, B. Rothenhäusler and W. Knoll, Surface plasmon microscopic characterization of external surfaces, *Journal of Applied Physics*, Vol. 66, (1989), 4832–4836.

[14] B. Rothenhäusler and W. Knoll, Interferometric determination of the complex wave vector of plasmon surface polaritons, *Journal of Optical Society of America B*, Vol. 5, (1988), 1401–1405.

[15] U. Fernandez, T. M. Fischer and W. Knoll, Surface-plasmon microscopy with grating couplers, *Optics Communications*, Vol. 102, (1993), 49–52.

What is claimed is:

1. A two-dimensional imaging surface plasmon resonance apparatus which comprises a sensor surface layer of a conductive material that can support a surface plasmon, a source of electromagnetic beams of two or more wave lengths that are collimated and illuminate a two-dimensional surface area from either the front or the backside of the sensor surface layer, and a detector for simultaneous, or pseudo simultaneous, detection of two or more waveiengths off reflected intensities from the two-dimensional surface areas, providing two or more two-dimensional images of the surface area, the two-dimensional images being a function of the effective refractive index at each point on the surface area.

2. The apparatus according to claim 1, wherein the conductive material is a free electron metal.

3. The apparatus according to claim 2, wherein the free electron metal is selected from the group consisting of gold, silver and aluminum.

4. The apparatus according to claim 1, wherein the sensor surface layer is a grating.

5. The apparatus according to claim 1, wherein a prism is provided as a support for the sensor surface layer.

6. The apparatus according to claim 5, wherein the sensor surface layer is supported on a planar transparent substrate plate, optically attached to the prism.

7. The apparatus according to claim 6, the planar transparent substrate plate is selected from glass and plastics, and the optical attachment is by an index matching fluid, gel or glue.

8. The apparatus according to claim 1, wherein the light source is selected from the group consisting of a) one or more monochromatic light sources, b) a glowing filament lamps, and c) a charge discharge lamp.

9. The apparatus according to claim 8, wherein the light source a) is selected from the group consisting of light emitting diodes and lasers, the light source b) is a Tungsten lamp, and the light source c) is a Xenon or Mercury lamp.

10. The apparatus according to claim 1, wherein the light from the light source is coupled into the sensor surface layer by a lens, a fiber optics, or a mirror.

11. The apparatus according to claim 1, wherein the light source provides a variable incident angle.

12. The apparatus according to claim 1, wherein the light of different wavelengths from the light source are pseudo-simultaneous impinging on the sensor layer by a rotating filter and are synchronized to the detector.

13. The apparatus according to claim 1, wherein the detector is selected from the group consisting of a two dimensional array camera, charge coupled device (CCD), charge injection device (CID), photo diode array detector (PDA), photomultiplier and a CMOS sensor.

14. The apparatus according to claim 1, wherein the detector has a mosaic filter.

15. The apparatus according to claim 1, wherein two or more detectors are provided, and these are fitted with beam splitters and filters, such as interference filters, to enable measurement of different spectral properties.

16. The apparatus according to claim 14, wherein the filter(s) is(are) adjustable.

17. The apparatus according to claim 1, wherein the detector(s) is(are) connected via an optical fiber bundle.

18. The apparatus according to claim 1, wherein the detector is a photographic film.

19. The apparatus according to claim 1, wherein a lens system, such as fixed focal length or a zoom, is provided to magnify or reduce the image.

20. The apparatus according to claim 1, wherein the apparatus operates with wavelengths at or close to the highest slope of the dip, either reflectance versus wavelength or reflectance versus the effective refractive index seen by the surface plasmon.

21. The apparatus according to claim 1, wherein the light that hits the detector is p-polarized by a polarizer.

22. The apparatus according to claim 1, wherein the two-dimensional images put together result in a color image.

* * * * *